United States Patent [19]

Boyce et al.

[11] Patent Number: 4,940,666
[45] Date of Patent: * Jul. 10, 1990

[54] PROCESS AND DEFINED MEDIUM FOR GROWTH OF HUMAN EPIDERMAL KERATINOCYTE CELLS

[75] Inventors: Stephen T. Boyce; Richard G. Ham, both of Boulder, Colo.

[73] Assignee: University Patents, Inc., Westport, Conn.

[*] Notice: The portion of the term of this patent subsequent to Jun. 16, 2004 has been disclaimed.

[21] Appl. No.: 939,579

[22] Filed: Dec. 9, 1986

Related U.S. Application Data

[63] Continuation of Ser. No. 514,178, Jul. 15, 1983, Pat. No. 4,673,649.

[51] Int. Cl.$^5$ .......................... C12N 5/00; C12N 5/02
[52] U.S. Cl. ............................ 435/240.2; 435/240.23; 435/240.25; 435/240.3
[58] Field of Search ........... 435/240.2, 240.21, 240.23, 435/240.25, 240.3, 240.31

[56] References Cited

PUBLICATIONS

Tsao et al., "Clonal Growth of Normal Human Epidermal Keratinocytes in a Defined Medium", J. Cellular Physiology, vol. 110, ©1982; pp. 219–229.

Kruse et al. (eds.); Tissue Culture, Ch. 8 "Freezing, Storage, and Recovery of cell Stocks", pp. 712–718, ©1973.

Hawley-Nelson et al., "Optimized Conditions for the Growth of Human Epidermal Cells in Culture", J. of Invest. Derm., ©1980; pp. 176–182.

Primary Examiner—Elizabeth C. Weimar
Attorney, Agent, or Firm—Curtis, Morris & Safford

[57] ABSTRACT

Disclosed are novel methods and materials for generating in vitro cultured populations of human epidermal keratinocyte cells having a characteristic colony-forming efficiency of greater than 20%. Novel media preparations and procedures are disclosed that permit isolation, serum-free primary culture and serum-free serial subculture of human epidermal keratinocytes. Also disclosed are procedures and products employing keratinocyte cells grown in serum-free conditions for medical application. i.e., skin grafting.

2 Claims, No Drawings

PROCESS AND DEFINED MEDIUM FOR GROWTH OF HUMAN EPIDERMAL KERATINOCYTE CELLS

This application is a continuation of application Ser. No. 514,178, filed July 15, 1983 now U.S. Pat. No. 4,673,6749.

BACKGROUND OF THE INVENTION

The present invention relates generally to the in vitro growth and differentiation of human epidermal keratinocytes. More particularly, the present invention is concerned with methods and materials for the initiation of primary cultures of human epidermal keratinocyte cells from human tissue, for the storage of these cells in viable frozen condition, for the establishment of secondary cultures recovered from frozen storage which enable serial propagation from the same primary culture, and for the use of these cells in products and procedures for the repair of injury to the skin.

Much of the historic development of cell culture has been based on the growth requirements and responses of fibroblast cells and closely related cell types. Fibroblasts are mesenchymal cells which, with collagen and elastic fibers in an extracellular matrix, compose loose ordinarily areolar connective tissue. Areolar connective tissue sheathes and penetrates muscles, nerves, and glands, and also forms the dermal tissue layer of the skin. Fibroblasts taken from tissues can be routinely cultivated either through many cell generations as karyotypically diploid cells or indefinitely as established cell lines. Thus, in many ways, conventional cell culture technology has been viewed as simulation in vitro of wound healing conditions.

For various reasons, normal epithelial cells and many of the tumors that develop from epithelial cells do not proliferate well in standard media and under conventional culture conditions. Epithelial cells, which cycle continuously in an uninjured body, form the covering tissue for nearly all the free surfaces of the body, including the epidermis of the skin. The basal layer of mammalian epidermis, separated by a basement membrane from the fibroblasts of the underlying dermis, is composed principally of dividing keratinocyte cells in various stages of differentiation. Some keratinocyte cells undergo terminal differentiation (i.e., move outward from the basal layer, increase in size, develop an envelope resistant to detergents and reducing agents, and eventually are shed from the surface). Because conventional tissue culture conditions have strongly favored multiplication of fibroblast-like cells, any epithelial cells that may be in a primary culture inoculum would tend to be overrun by fibroblast cells.

The ability to culture viable layers of nondifferentiated human epidermal keratinocyte cells with minimal fibroblast overgrowth would have considerable application to medical procedures for wound healing. As one example, when human tissue has been severely damaged due to a severe burn, it is necessary to cover the damaged area to reduce fluid loss, prevent infection and reduce scarring. Because autografts are painful and difficult when damage is extensive, other functioning substitutes for skin have been sought, i.e., homografts (skin transplants from live donors or from skin preserved in skin banks), modified skin from animals, synthetic polymeric structures, reconstituted collagen films, and biodegradable synthetic membranes, such as described in Yannas, et al., U.S. Pat. No. 4,060,081.

Many of these skin substitutes have the potential for inducing inflammatory response in a patient caused by rejection of some antigenic substance in the skin substitute by the immune system. Further, it is often the case that a patient with extensive or severe injury suffers considerable risk of infection and death due to immune depression associated with the second and third weeks of a skin graft. Whether an autograft, homograft or skin substitute is employed to cover the damaged tissue, a graft may be unavailing to a patient succumbing to infection unless the skin repair is rapid enough to reduce exposure to the outside environment.

Recent studies have focused on the development of nutritionally optimized and readily defined and reproducible media and culture conditions which may provide a selective advantage to epithelial cells. The ability to culture layers of keratinocyte cells of the skin in vitro from a small inoculum could replace the requirement for autografts in present wound repair treatments.

Early research on the propagation of epithelial keratinocyte cells indicated that disaggregated epidermal cells only grew in monolayers to a very limited extent, and could not be satisfactorily subcultured. In a significant early study, clonal growth of human epidermal keratinocytes was obtained by plating human skin cells with a semi-confluent feeder layer of lethally irradiated 3T3 fibroblast cells which prevented fibroblast overgrowth and promoted multiplication of human keratinocytes in Delbecco's modified medium (DME) supplemented with hydrocortisone (HC) and 20% whole fetal bovine serum (wFBS). The human diploid keratinocytes grown in this system had a finite culture lifetime and low plating efficiency in primary culture (0.1 to 1.0%). On subculture, the plating efficiency rose only occasionally to 10% but was most often in the range of 1 to 5%. Only a range of two to six serial transfers were possible in this system; and, in the absence of 3T3 cells, the human keratinocytes could not even initiate colony formation. [See, Rheinwald, J. G., et al., Cell, 6, pp. 331-334 (1975)].

It was noted in a later study that keratinocytes grown in the lethally irradiated 3T3 cell system were enhanced by the presence of epidermal growth factor (EGF) in the medium. [Rheinwald, J. G., et al., Nature, 265, pp. 421-424 (1977)].

Further definition of an optimal medium for growth of human keratinocytes revealed that only the primary culture of keratinocytes required the presence of the 3T3 fibroblast cells [Peehl, D. M., et al., *In Vitro*, Vol. 16(6), pp. 516-525 (1980)]. Following the establishment of primary human keratinocyte cultures by the Rheinwald, et al., 3T3 feeder layer method described above, the 3T3 cells were removed on day 3 of culture with ethylene diamine tetraacetic acid (EDTA). Various commercially available test media, each supplemented with hydrocortisone, whole fetal bovine serum and conditioned for 24 hours by irradiated 3T3 cells, were added to the cultures. Substantial multiplication of human keratinocytes occurred only in conditioned Medium 199, described in Morgan, J. F., et al., *Proceedings in the Society of Experimental Biological Medicine*, 73, pages 1-8 (1950), in which the stratified keratinocyte colonies grew to confluency and could be subcultured. When cells from the primary culture were inoculated in unconditioned Medium 199, supplemented with an increased concentration of hydrocortisone, whole fetal bovine serum, and pituitary extract fractions, similar growth was achieved, indicating that human keratinocytes, after the primary culture was established, did not require special conditioning factors from fibroblasts for clonal growth and differentiation in culture.

Subsequent studies indicated that commercially available medium F12 eliminated the need for pituitary extract and allowed dialyzed fetal bovine serum protein to be used in place of whole serum for clonal growth media. Adjustments of the composition of medium F12 for optimal clonal growth resulted in a new medium, MCDB151, which supported clonal growth of human keratinocytes with hydrocortisone and fetal bovine serum protein. Optimal growth of human keratinocytes occurred at a very low concentration of calcium ion (0.03 mM) which causes the colonies to remain as monolayers, rather than stratifying as they do in the presence of higher levels of calcium. While medium MCDB151 supported clonal growth of human epidermal keratinocytes with 1.0 mg/ml of fetal bovine serum protein as the only macromolecular supplement, the Rheinwald, et al., feeder layer technique was required for establishment of primary cultures, and subcultures showed a low colony-forming efficiency [See, Peehl, D. M., 5 et al., *In Vitro*, Vol. 16(6), pp. 526–538 (1980)].

To develop a medium containing no deliberately added undefined supplements and capable of supporting colony formation of normal human epidermal keratinocytes, hormone and growth factor replacement in the medium was studied [Tsao, M. C., et al., *J. Cell. Physiol.*, 110, pp. 219-229 (1982)]. A new basal medium, MCDB152, was formulated by addition of the trace element supplement from medium MCDB104 [McKeehan, W. L., et al., *In Vitro*, 13, pages 399-416 (1977)] to medium MCDB151. The ingredients of basal medium MCDB152 therefore included the following: arginine, $1.0 \times 10^{-3}$ M; cysteine, $2.4 \times 10^{-4}$ M; glutamine, $6.0 \times 10^{-4}$ M; histidine, $8.0 \times 10^{-5}$ M; isoleucine, $1.5 \times 10^{-5}$ M; leucine, $5.0 \times 10^{-4}$ M; lysine, $1.0 \times 10^{-4}$ M; methionine, $3.0 \times 10^{-5}$ M; phenylalanine, alanine, $3.0 \times 10^{-5}$ M; threonine, $1.0 \times 10^{-4}$ M; tryptophan, $1.5 \times 10^{-5}$ M; tyrosine, $1.5 \times 10^{-5}$ M; valine, $3.0 \times 10^{-4}$ M; alanine, $1.0 \times 10^{-4}$ M; asparagine, $1.0 \times 10^{-4}$ M; aspartate, $3.0 \times 10^{-5}$ M; glutamate, $1.0 \times 10^{-4}$ M; glycine, $1.0 \times 10^{-4}$ M; proline, $3.0 \times 10^{-4}$ M; serine, $6.0 \times 10$ M; biotin, $6.0 \times 10^{-8}$ M; folate, $1.8 \times 10^{-6}$ M; lipoate, $1.0 \times 10^{-6}$ M; niacinamide, $3.0 \times 10^{-7}$ M; pantothenate, $1.0 \times 10^{-6}$ M; pyridoxine, $3.0 \times 10^{-7}$ M; riboflavin, $1.0 \times 10^{-7}$ M; thiamin, $1.0 \times 10^{-6}$ M; Vitamin B$_{12}$, $3.0 \times 10^{-7}$ M; adenine, $1.8 \times 10^{-4}$ M; thymidine, $3.0 \times 10^{-6}$ M; acetate, $3.7 \times 10^{-3}$ M; choline, $1.0 \times 10^{-4}$ M; glucose, $6.0 \times 10^{-3}$ M; i-inositol, $1.0 \times 10^{-4}$ M; putrescine, $1.0 \times 10^{-6}$ M; pyruvate, $5.0 \times 10^{-4}$ M; calcium, $3.0 \times 10^{-5}$ M; magnesium, $6.0 \times 10^{-4}$ M; potassium, $1.5 \times 10^{-3}$ M; sodium, $1.5 \times 10^{-1}$ M; chloride, $1.3 \times 10^{-1}$ M; phosphate, $2.0 \times 10^{-3}$ M; sulfate, $4.5 \times 10^{-6}$ M; copper, $1.1 \times 10^{-8}$ M; iron, $1.5 \times 10^{-6}$ M; zinc, $3.5 \times 10^{-6}$ M; bicarbonate $1.4 \times 10^{-2}$ M; carbon dioxide, 5%; HEPES, $2.8 \times 10^{-2}$ M; phenol red, $3.3 \times 10^{-6}$ M; manganese, $1.0 \times 10^{-9}$ M; molybdenum, $1.0 \times 10^{-9}$ M; nickel, $5.0 \times 10^{-10}$ M; selenium, $3.0 \times 10^{-8}$ M; silicon, $5.0 \times 10^{-7}$ M; tin, $5.0 \times 10^{-10}$ M; and vanadium, $5.0 \times 10^{-9}$ M. This new basal medium was further supplemented to create the defined medium for growth of human keratinocytes, with epidermal growth factor, 5 ng/ml; transferin, 10 µg/ml; insulin, 5 µg/ml; hydrocortisone, $1.4 \times 10^{-6}$ M; ethanolamine, $1.0 \times 10^{-5}$ M; phosphoethanolamine, $1.0 \times 10^{-5}$ M; and progesterone, $2.0 \times 10^{-9}$ M.

In this study, the Rheinwald, et al. feeder layer technique was employed to establish primary cultures, and to suppress overgrowth of fibroblasts and enhance growth of keratinocytes. Clonal growth experiments were performed in the supplemented medium MCDB152. Previous requirements for dialyzed serum and bovine pituitary extract were replaced with the mixture of supplements previously identified. The replacement of whole bovine pituitary extract with ethanolamine and phosphoethanolamine in this study removed the last deliberately added undefined supplement. These researchers were able to obtain clonal growth of human epidermal keratinocytes in a chemically defined medium with a low ratio (1:2) of iron concentration ($1.5 \times 10^{-6}$ M) to zinc concentration ($3 \times 10^{-6}$ M), with 10 µg/ml transferrin.

Following the initiation of keratinocyte growth in the primary culture, cells in this study were transferred to MCDB152 with supplements. Despite the absence of undefined elements in this medium, several problems were revealed during the course of experimentation. Variable growth of keratinocytes was achieved in MCDB152, but the researchers could not transfer the culture to a third vessel and obtain a viable culture. After the first subculture, the Tsao, et al. researchers achieved a very small colony-forming efficiency (less than 2%). Further, good growth was only obtained in the defined media when the cellular inoculum was prepared from a primary culture using the Rheinwald, et al. technique of 3T3 feeder cells. The cells could not be frozen for storage and subsequently recovered as viable culture-producing cells.

In an alternative attempt to overcome the technical limitations inherent in the Rheinwald, et al. 3T3 feeder layer system for keratinocyte culture, a culture system was developed using human fibronectin. Keratinocytes were established in a primary culture in Delbecco's Modified Eagle s Medium supplemented with 20% fetal bovine serum, hydrocortisone, penicillin G, and streptomycin. The epithelial cells were plated on fibronectin coated plates, requiring ten-fold larger plating densities than the Rheinwald, et al. technique to obtain comparable colony formation. In this system, fibroblast-like cells were apparent in many plates but overgrowth did not occur [See, Gilchrest, B. A., et al., *Cell Biology International Reports*, Vol. 4, No. 11, pp. 1009–1016 (1980)].

In later related studies human keratinocytes plated on fibronectin-coated cell culture dishes were grown in a cell culture medium consisting of medium 199 with epidermal growth factor, tri-iodothyronine, hydrocortisone, Cohn Fraction IV, insulin, transferin, bovine brain extract, and trace elements. The researchers determined that brain extract was necessary to preserve normal keratinocyte morphology and protein production in this system. [See, Maciag, T., et al., *Science*, 211, pp. 1452-1454 (1981); Gilchrest, et al., *J. Cellular Physiology*, 112, pp. 197-206 (1982)]. The Maciag/Gilchrest culture system, characterized by the presence of undefined macromolecular ingredients, i.e., brain extract, Cohn fraction IV and serum, shows no advantage over the Rheinwald, et al. system due to requirements for very high inoculation densities and fibronectin-coated culture vessels in order to achieve an increase in cell numbers per unit time.

From the above description of the state of the art, it will be apparent that there continues to exist a need in the art for methods and materials for securing serum-free production of human epidermal keratinocyte cells. The attempts described thus far have enabled growth of keratinocyte cells from the primary inoculum, but rely on serum components introduced by the feeder layer technique or the use of bovine serum protein in culture medium.

There thus remains a need in the art for materials and methods to provide (1) a source of human epidermal keratinocyte cells for biological research and medical applications grown in serum-free conditions and having a high colony-forming efficiency in serial subculture; (2) a source of human keratinocytes which has no exposure to serum, thereby eliminating the possibility for inducing inflammatory response when used in medical applications; and (3) a source of human keratinocytes having a velocity or efficiency of growth for use in skin grafts thereby contributing to reduced trauma and infection in a patient during the period of exposure of the injury to the environment.

BRIEF SUMMARY

According to one aspect of the invention, there is provided a basal nutrient medium MCDB153 suitable for (a) growth of a population of human keratinocyte cells in a primary culture; or (b) supporting a viable population of human keratinocyte cells in frozen storage; or (c) clonal growth of a population of human epidermal keratinocyte cells.

A stock culture medium suitable for growth of a population of human keratinocyte cells in a primary culture may comprise: MCDB153; epidermal growth factor at a concentration range of 1.0 ng/ml to 25.0 ng/ml; and insulin at a concentration range of 0.5 µg/ml to 50.0 µg/ml. This stock culture medium may further comprise one or more of the following supplements: hydrocortisone at a concentration range of 0.14 µM to 28.0 µM; ethanolamine at a concentration of 0.01 mM to 1.0 mM; phosphoethanolamine at a concentration range of 0.01 mM to 1.0 mM; calcium chloride at a concentration range of 0.03 mM to 1.0 mM; and whole bovine pituitary extract at a concentration range of 7.0 µg/ml to 700.0 µg/ml. Preferred concentrations of the supplements in the stock culture medium are the following: epidermal growth factor at a concentration of 10 ng/ml; insulin at a concentration of 5 µg/ml; hydrocortisone at a concentration of 1.4 µM; ethanolamine at a concentration of 0.1 mM; phosphoethanolamine at a concentration of 0.1 mM; calcium chloride at a concentration of 0.1 mM; and whole bovine pituitary extract at a concentration of 70 µg/ml. The stock culture media of the present invention allow the multiplication of human keratinocytes for use in routine experimentation or as a source of secondary inocula for stock cultures or clonal growth experiments.

In another of its aspects, the present invention provides a medium suitable for supporting a viable population of human keratinocyte cells in frozen storage. The components of this medium comprise: MCDB153; and epidermal growth factor at a concentration range of 1.0 ng/ml to 25.0 ng/ml. This storage medium can be supplemented with one or more of the following: hydrocortisone at a concentration range of 0.14 µM to 28.0 µM; calcium chloride at a concentration range of 0.03 mM to 1.0 mM; whole bovine pituitary extract at a concentration range of 70.0 µg/ml to 2800.0 µg/ml; whole bovine fetal serum at a concentration range of 2.0% v/v to 50.0% v/v; and dimethylsulfoxide at a concentration range of 2.0% v/v to 20 0% v/v. Concentrations of the individual supplements are preferably the following: epidermal growth factor at a concentration of 10 ng/ml; hydrocortisone at a concentration of 1.4 µM; calcium chloride at a concentration of 0.1 mM; whole bovine pituitary extract at a concentration of 700 µg/ml; whole bovine fetal serum at a concentration of 20.0% v/v; and dimethylsulfoxide at a concentration of 10% v/v.

Use of this frozen storage medium permits the frozen storage of human keratinocyte cell cultures in the absence of serum, and further permits recovery of viable cells as inoculum for secondary cultures and clonal growth assays. The use of this medium and its ability to store, in a frozen condition, viable keratinocyte cells enable the accumulation of a virtually unlimited supply of human epidermal keratinocyte cells for research and medical use.

In another of its aspects, the present invention provides a medium suitable for clonal growth of a population of human epidermal keratinocyte cells. This clonal growth medium comprises: MCDB153; epidermal growth factor at a concentration range of 1.0 ng/ml to 25.0 ng/ml; and insulin at a concentration range of 0.5 µg/ml to 50.0 µg/ml. The clonal growth medium may be further supplemented with one or more of the following: hydrocortisone at a concentration range of 0.14 µM to 28.0 µM; ethanolamine at a concentration range of 0.01 mM to 1.0 mM; phosphoethanolamine at a concentration range of 0.01 mM to 1.0 mM; calcium chloride at a concentration range of 0.03 mM to 1.0 mM; and, where strictly defined conditions are not essential, whole bovine pituitary extract at a concentration range of 7.0 µg/ml to 700.0 µg/ml. Preferred concentrations of the supplemental components are the following: epidermal growth factor at a concentration of 5.0 ng/ml; insulin at a concentration of 5.0 µg/ml; hydrocortisone at a concentration of 1.4 µM; ethanolamine at a concentration of 0.1 mM; phosphoethanolamine at a concentration of 0.1 mM; calcium chloride at a concentration in the range of 0.3–1.0 mM; and whole bovine pituitary extract at a concentration of 70 µg/ml.

There is thus provided a completely defined medium for the growth of human keratinocyte cells in the absence of serum. Bovine pituitary extract is not needed for a single clonal passage in the defined medium, but is beneficial for the initiation of primary cultures and repeated subculture under serum-free conditions.

The use of the defined supplements in the basal media in place of serum which binds calcium and thereby contributes to total calcium in the medium enables the utilization of lower calcium concentration in the media for stock culture, frozen storage or clonal growth. The lower calcium concentration provides a significant advantage over media available in the prior art because it tends to improve cellular multiplication without causing significant terminal differentiation.

In another of its aspects, the present invention provides a population of human epidermal keratinocyte cells grown in the aforementioned media for growth in stock culture or frozen storage and having a colony-forming efficiency greater than 20% in the clonal growth medium. Also provided is a population of human epidermal keratinocyte cells in a frozen state in the aforementioned medium for frozen storage and having a colony-forming efficiency of greater than 20% in the clonal growth medium. These cell populations may be grown in a totally serum-free environment to form a monolayer of cells in the clonal growth medium capable of a variety of uses including use in a system to enable skin grafting over injuries or burns.

In yet another of its aspects, the present invention provides for an improvement in a method for establishing a population of human epidermal keratinocyte cells in vitro wherein the cells are obtained by treatment of human foreskin tissue to separate the epidermal tissue layer from the dermal tissue layer. The improvement involves a step comprising growing the keratinocyte cells in the above-described stock culture or clonal growth media. Further, there is provided an improvement in methods for storing a viable population of human epidermal keratinocyte cells in frozen condition, comprising storing the keratinocyte cells in the above-described frozen storage medium.

Yet another improvement is provided in a method for obtaining clonal growth of a population of human epidermal keratinocyte cells. The improvement comprises growing the keratinocyte cells in the abovedescribed clonal growth medium.

These methods enable the establishment of cultures of human keratinocyte cells which can be employed in skin grafting procedures or as a model for further medical and biological study. Cultures of keratinocyte cells thus established may be serially subcultured to produce monolayers of cells for immediate use, kept for short periods as readily available stock cultures, or stored for long periods of time as frozen cultures.

As a further aspect, the present invention provides a method for engrafting a layer of epidermal cells onto damaged skin tissue. This method entails applying to the damaged tissue a population of human epidermal keratinocyte cells grown in the stock culture medium before or after storage in the frozen storage medium, both populations having a colony-forming efficiency of greater than 20% in the clonal growth medium.

In still a further aspect of the invention, there is provided a product having the capacity to promote reestablishment of epithelial tissue onto damaged tissue comprising: (1) a population of human epidermal keratinocyte cells grown in the basal medium MCDB, the stock culture medium or frozen storage medium described above and having a colony-forming efficiency of greater than 20% in the clonal growth medium; and (2) a suitable support matrix vehicle for transporting the cell population to the site of the damaged tissue. The vehicle for transport of the cells may be a biodegradable matrix or a multilayer collagenous membrane.

Also provided is a method for encouraging repair of damaged skin tissue comprising applying a cell and support matrix vehicle product as described above to the damaged tissue. A membrane for use in this method should preferably contain a collagen-like material and be permeable to moisture. Such a multi-layer membrane has been disclosed in Yannas, et al., U.S. Pat. No. 4,060,081.

Use of the human epidermal keratinocyte cell populations of the present invention in a method for skin grafting will enable a patient with damaged tissue to supply his own cells for culturing. Use of the methods and products of the present invention will therefore obviate the need for removal of large areas of tissue from the patient as required by conventional autografting techniques reducing trauma to the patient and will avoid provocation of immune responses to foreign antigenic substances occasioned by use of the homograft and synthetic techniques.

Other aspects and advantages of the invention will become apparent upon consideration of the following detailed description of preferred embodiments thereof.

DETAILED DESCRIPTION

The novel methods and materials provided by the present invention are illustrated in the following examples which relate to manipulations involved in employing the basal medium MCDB153 for preparation of primary cultures, storage and clonal growth of human epidermal keratinocytes. More particularly, Example 1 is directed to the materials and procedure for preparation of basal medium MCDB153 and addition of supplements. Examples 2–4 are directed to the isolation and multiplication of a primary culture of human keratinocytes, the preparation of a culture of keratinocytes for frozen storage, and the multiplication of secondary cultures of keratinocytes. Clonal growth assays of human keratinocytes are described in Example 5. Example 6 describes preliminary experimental procedures for attachment of keratinocytes to a nonantigenic biodegradable membrane for use in skin grafting.

EXAMPLE 1

A Preparation of Basal Medium

Except as noted otherwise, all biochemicals and hormones are from Sigma Chemical Company and all inorganic chemicals are from Fisher Scientific. Epidermal growth factor (EGF) may be prepared according to the procedure of Savage, C., et al., *J.Biol.Chem.*, 247, pp. 7609–7611 (1972), or purchased, e.g., from Bethesda Research Labs.

Table III below details the concentrations of components in the basal medium MCDB153.

TABLE III

| Stock | Component | Concentration in Final Medium mg/l | mol/l |
|---|---|---|---|
| 1 | Arginine.HCl | 210.7 | $1.0 \times 10^{-3}$ |
|  | Histidine.HCl.H$_2$O | 16.77 | $8.0 \times 10^{-5}$ |
|  | Isoleucine allo-free | 1.968 | $1.5 \times 10^{-5}$ |
|  | Leucine | 65.6 | $5.0 \times 10^{-4}$ |
|  | Lysine.HCl | 18.27 | $1.0 \times 10^{-4}$ |
|  | Methionine | 4.476 | $3.0 \times 10^{-5}$ |
|  | Phenylalanine | 4.956 | $3.0 \times 10^{-5}$ |
|  | Threonine | 11.91 | $1.0 \times 10^{-4}$ |
|  | Tryptophan | 3.06 | $1.5 \times 10^{-5}$ |
|  | Tyrosine | 2.718 | $1.5 \times 10^{-5}$ |
|  | Valine | 35.13 | $3.0 \times 10^{-4}$ |
|  | Choline | 13.96 | $1.0 \times 10^{-4}$ |
|  | Serine | 63.06 | $6.0 \times 10^{-4}$ |
| 2 | Biotin | 0.0146 | $6.0 \times 10^{-8}$ |
|  | Calcium pantothenate | 0.258 | $1.0 \times 10^{-6}$ |
|  | Niacinamide | 0.03663 | $3.0 \times 10^{-7}$ |
|  | Pyridoxine.HCl | 0.06171 | $3.0 \times 10^{-7}$ |
|  | Thiamine.HCl | 0.3373 | $1.0 \times 10^{-6}$ |
|  | Potassium chloride | 111.83 | $1.5 \times 10^{-3}$ |
| 3 | Folic acid | 0.79 | $1.8 \times 10^{-6}$ |
|  | Na$_2$HPO$_4$.7H$_2$O | 536.2 | $2.0 \times 10^{-3}$ |
| 4a | CaCl$_2$.2H$_2$O | 4.411 | $3.0 \times 10^{-5}$ |
| 4b | MgCl$_2$.6H$_2$O | 122.0 | $6.0 \times 10^{-4}$ |
| 4c | FeSO$_4$.7H$_2$O | 1.39 | $5.0 \times 10^{-6}$ |
| 5 | Phenol red | 1.242 | $3.3 \times 10^{-6}$ |
| 6a | Glutamine | 877.2 | $6.0 \times 10^{-3}$ |
| 6b | Sodium pyruvate | 55.0 | $5.0 \times 10^{-4}$ |
| 6c | Riboflavin | 0.03764 | $1.0 \times 10^{-7}$ |
| 7 | Cysteine.HCl.H$_2$O | 42.04 | $2.4 \times 10^{-4}$ |
| 8 | Asparagine | 15.01 | $1.0 \times 10^{-4}$ |
|  | Proline | 34.53 | $3.0 \times 10^{-4}$ |
|  | Putrescene | 0.1611 | $1.0 \times 10^{-6}$ |
|  | Vitamin B$_{12}$ | 4.07 | $3.0 \times 10^{-7}$ |
| 9 | Alanine | 8.91 | $1.0 \times 10^{-4}$ |
|  | Aspartic acid | 3.99 | $3.0 \times 10^{-5}$ |

TABLE III-continued

| Stock | Component | Concentration in Final Medium | |
|---|---|---|---|
| | | mg/l | mol/l |
| | Glutamic acid | 14.71 | $1.0 \times 10^{-4}$ |
| | Glycine | 7.51 | $1.0 \times 10^{-4}$ |
| 10 | Adenine | 24.32 | $1.8 \times 10^{-4}$ |
| | Inositol | 18.02 | $1.0 \times 10^{-4}$ |
| | Lipoic acid | 0.2063 | $1.0 \times 10^{-6}$ |
| | Thymidine | 0.7266 | $3.0 \times 10^{-6}$ |
| | $CuSO_4 \cdot 5H_2O$ | 0.00249 | $1.0 \times 10^{-8}$ |
| L | Copper | | $1.0 \times 10^{-9}$ M |
| | Manganese | | $1.0 \times 10^{-9}$ M |
| | Molybdenum | | $1.0 \times 10^{-9}$ M |
| | Nickel | | $5.0 \times 10^{-10}$ M |
| | Selenium | | $3.0 \times 10^{-8}$ M |
| | Silicon | | $5.0 \times 10^{-7}$ M |
| | Tin | | $5.0 \times 10^{-10}$ M |
| | Vanadium | | $5.0 \times 10^{-9}$ M |
| | Zinc | | $5.0 \times 10^{-7}$ M |
| Not Stock | | | |
| | Glucose | 1081 | $6.0 \times 10^{-3}$ |
| | Sodium chloride | 7599 | $1.3 \times 10^{-1}$ |
| | Sodium acetate | 500 | $3.7 \times 10^{-3}$ |
| | HEPES | 6600 | $2.8 \times 10^{-2}$ |
| | Sodium bicarbonate | 1176 | $1.4 \times 10^{-2}$ |
| | Water | — | — |

One liter of medium MCDB153 is prepared by the following procedures. To 800 ml distilled water is added 10 ml each of Stocks 1, 2, 6b, 6c, 7, 8, 9, and 10; 20 ml Stock 3; 1 ml Stock 5; and 60 ml Stock 6a. While stirring, 1.081 g glucose, 7.599 g sodium chloride, 0.5 g sodium acetate and 6.6 g HEPES are added to the solution. This solution is adjusted to pH 7.4 with 4.0N NaOH and sodium bicarbonate is then added in an amount of 1.176 g. Triple-distilled water is added to a final volume of 983 ml. This solution may be stored non-sterilely if frozen at −20° C. in any convenient volume.

Complete basal medium MCDB153, normally prepared in small amounts just before use, can be stored at 4° C. for a few days if necessary. To each 98.3 ml of the above solution, the following are added with stirring: 0.50 ml stock 4c; 0.10 ml stock 4b; 0.10 ml stock 4a; and 1.0 ml stock L. The completed medium is sterilized by filtration with a detergent free 0.2 μm pore size filter unit (Nalge Co., No. 450-0020) to avoid possible loss of precipitated iron from stock 4c on the sterilizing filter. Alternatively, sterile stock 4c can be added aseptically after the medium has been filter sterilized.

B. Preparation of Supplemented Medium

Prior to its addition to basal medium, sterile lyophilized EGF is dissolved in sterile solution A (a saline solution containing 30 mM HEPES-NaOH buffer, 10 mM glucose, 3 mM KCl, 130 mM NaCl, 1 mM $Na_2HPO_4 \cdot 7H_2O$, and 0.0033 mM phenol red, with its pH adjusted to 7.6 with 4.0N NaOH), either at 5 μg/ml or at 10 μg/ml. Insulin for supplementation is dissolved in aqueous 12 mM HCl at 5 mg/ml (which yields a solution whose pH is approximately 2), and filter sterilized. Hydrocortisone is dissolved in absolute ethanol at 0.5 mg/ml and filter sterilized. Ethanolamine and phosphoethanolamine are dissolved separately in solution A at a concentration of 0.1M and filter sterilized.

Whole bovine pituitary extract (wBPE) is prepared by homogenizing 105 g of fresh mixed sex adult bovine pituitaries in 250 ml 0.15M NaCl for 5 minutes at 4° C. in a Waring blender operated at maximum speed. The homogenate is stirred for 90 minutes at 4° C. and centrifuged at 13,000×g for 10 minutes. The resultant supernatant is filtered in a Buchner funnel through Whatman No. 1 filter paper. Protein content of wBPE, determined by the method of Lowry, et al., J.Biol.Chem., 193, pp. 265–276 (1951) with bovine serum albumin as a standard, is typically slightly less than 14 mg/ml. After centrifugation at 20,000×g for 10 minutes, the supernatant is sequentially filtered through 0.8 μm and 0.45 μm pore-size detergent-free filters, and then sterilized by passage through a 0.2 μm pore-size detergent-free filter.

Table IV indicates the supplementation of basal medium MCDB153 for stock cultures, frozen storage, and clonal growth of human keratinocytes.

TABLE IV

| | Stock Cultures | Frozen Storage | Clonal Growth |
|---|---|---|---|
| EGF | 10 ng/ml | 10 ng/ml | 5 ng/ml |
| Insulin | 5 μg/ml | 0 | 5 μg/ml |
| Hydrocortisone | 1.4 μM (0.5 μg/ml) | 1.4 μM (0.5 μg/ml) | 1.4 μM (0.5 μg/ml) |
| Ethanolamine | 0.1 mM | 0 | 0.1 mM |
| Phosphoethanolamine | 0.1 mM | 0 | 0.1 mM |
| $CaCl_2$ (final concentration) | 0.1 mM | 0.1 mM | 0.03–1.0 mM |
| wBPE | 70 μg/ml (0.5% v/v) | 700 μg/ml (5% v/v) | 0 |
| DMSO | 0 | 10% v/v | 0 |

In supplemented MCDB153 for stock cultures and frozen storage, whole bovine pituitary extract (wBPE) is the only undefined component. The clonal growth medium contains no deliberately added undefined components. Where chemical definition is not critical, 70 μg/ml wBPE can be added to the clonal growth medium.

In media for stock cultures and clonal growth, ethanolamine and phosphoethanolamine are used at concentrations that are ten times those previously employed for human keratinocytes [see Tsao, supra] and substantially higher than reported for various other cell types.

Medium MCDB153 differs from media in the prior art in its increased level of ferrous iron $5 \times 10^{-6}$ M) and decreased level of zinc $5 \times 10^{-7}$ M). These concentrations eliminate any requirement for transferrin, the most undefined supplement of MCDB152.

EXAMPLE 2

Human keratinocyte cultures are initiated from human foreskin tissue removed during routine circumcision of newborn male infants. Immediately after excision, the foreskins are placed in solution A described in Example 1 plus penicillin, streptomycin, and Fungizone and are stored at 4° C. Within 48 hours after circumcision, cultures are initiated. Four to six foreskins are generally pooled for use in establishing primary cultures, and the steps of primary culture preparation are performed under sterile conditions:

(1) Each foreskin is placed in sterile solution A. Subcutaneous connective tissue is removed.

(2) The tissue is washed in 5% v/v Dettol and rinsed three times in sterile solution A.

(3) Small, 2 mm square pieces of tissue in solution A are centrifuged at 250×g for 5 minutes.

(4) The supernatant is aspirated and the tissue pieces are resuspended in 15 ml of a solution of 0.25% collagenase (Worthington No. 4196 CLS40S239) plus 10% (v/v) wBPE in MCDB153. 7.5 ml of the suspension is transferred to each of two 60 mm petri dishes (Lux No.

5220) and placed into a 37° C. incubator with 5% $CO_2$ and saturated humidity for 90-120 minutes or until epidermis is readily removable from dermis.

(5) While the collagenase digestion is in progress, tissue culture flasks of 25, 75, or 150 $cm^2$ area are prepared. A preparation from 4 to 6 foreskins typically requires 600-750 $cm^2$ of culture surface and 120-150 ml of supplemented medium. For each 100 ml of supplemented stock culture medium (Table IV), the following components are sterilely added together: 98 ml MCDB153; 0.07 ml $CaCl_2$ (0.1 M); 0.1 ml EGF (10 μg/ml); 0.1 ml insulin (5 mg/ml); 0.1 ml hydrocortisone (0.5 mg/ml); 0.1 ml ethanolamine (0.1M); 0.1 ml phosphoethanolamine (0.1M); 0.5 ml wBPE (14 mg/ml protein); and 1.0 ml of a solution of 100 units/ml penicillin, 100 μg/ml streptomycin, and 0.25 μg/ml Fungizone (Gibco Cat. No. 600-5245). After gentle mixing, 24 ml of supplemented medium are added to each 150 $cm^2$ flask, 14.5 ml to each 75 $cm^2$ flask, or 4.8 ml to each 25 $cm^2$ flask. The flasks are placed into a 37° C. incubator gassed with 5% $CO_2$ in air saturated with water vapor and the caps are loosened on the flasks to allow the medium to equilibrate with the 5% $CO_2$.

(6) The collagenase digestion mixture of Step (4) is removed from the 37° C. incubator after 90-120 minutes. The collagenase solution is aspirated and replaced with solution A. For each piece of tissue, the epidermis is removed from the dermis as an intact sheet with sterilized forceps.

(7) The epidermal layers are then placed in solution A at room temperature.

(8) Solution A is gently aspirated from the epidermal fragments. 6 ml of a solution of 0.025% trypsin (w/v) and 0.01% EDTA (w/v) in solution A is added and the epidermal fragments are gently pipetted for 3-4 minutes to release individual cells. The cell suspension is withdrawn from the remaining tissue fragments, placed in a sterile centrifuge tube, and centrifuged at 250×g for 5 minutes.

(9) 6 ml of a solution containing 0.1% (w/v) soybean trypsin inhibitor (STI) and 10% (v/v) Vitrogen 100 (Collagen Corp., Palo Alto, Calif.) in MCDB153 is added to the epidermal pieces left in the petri dish. The pellet from the centrifugation of Step (8) is resuspended in 6 ml of the same solution. (Alternatively, if strictly serum-free conditions are not essential, 10% whole fetal bovine serum may replace 0.1% STI plus 10% collagen.) The pellet is resuspended by gentle pipetting. Individual cells from the epidermal pieces in the petri dish are released by repeating the pipette pumping process. Only the resulting cell suspension is transferred from the dish to the tube containing the resuspended pellet and centrifuged at 250×g for 5 minutes.

(10) The trypsin-inhibitor (or serum) solution is aspirated from the pellet and the pellet is resuspended in 2-3 ml of the supplemented stock culture medium and gently pipetted until the pellet is dispersed into a suspension of single cells. The cells are counted and the cell density is adjusted to $5 \times 10^5$ cells/ml. 1.0 ml of cells is inoculated into each 150 $cm^2$ flask, 0.5 ml into each 75 $cm^2$ flask, and 0.2 ml into each 25 $cm^2$ flask that was prepared in Step (5) and equilibrated in the cell culture incubator.

(11) The inoculated flasks are shaken gently and incubated at 37° C. in an atmosphere of 5% $CO_2$ in air saturated with water vapor, with the caps loosened for equilibration. After 48 hours the medium is removed and replaced with fresh medium of the same composition, without the antibiotics, without agitating or rinsing the cultures. At 5-7 days after inoculation, the medium is removed, the cultures are washed twice with solution A, and fresh medium is added. This procedure is repeated again at 10-12 days after inoculation (or 24 hours before harvest of the primary cultures).

The cultures that develop under these conditions are composed of colonies that grow as a single layer of cells on the culture surface and do not stratify or exhibit terminal differentiation. As the primary cultures mature, cellular multiplication tends to stop at a time when the colonies have not yet contacted one another to form a confluent monolayer. The cultures are judged to be ready for harvesting when 2-8 cell satellite colonies begin to appear but many mitotic cells remain visible in the larger colonies. This degree of development normally requires 10-14 days.

EXAMPLE 3

When the primary cultures are mature, the cells are removed from the culture flask and stored frozen and at liquid nitrogen temperature. The medium used for serum-free frozen storage is MCDB153 supplemented with 5% (v/v) wBPE, 0.1 mM $Ca++$, 10 ng/ml EGF, 0.5 μg/ml hydrocortisone, and 10% (v/v) DMSO (Table II). Alternatively, MCDB153 supplemented with 20% whole fetal bovine serum, 0.5% (v/v) wBPE, 0.1 mM $Ca++$, 10 ng/ml EGF, 0.5 μg/ml hydrocortisone and 10% (v/v) DMSO can also be used with good results. The growth medium is aspirated from the cultures, and the cells are washed twice with solution A. The cells are then exposed to 0.025% trypsin (w/v) and 0.01% EDTA (w/v) in solution A (approximately 2.5 ml per flask $cm^2$) for 30-60 seconds. The solution is removed by aspiration and the flasks with the caps secured tightly are left at room temperature. The cultures are examined with an inverted microscope after 3-4 minutes. If less than 50% of the cells have detached, the trypsin-EDTA digestion is continued for successive 3 minute periods until more than 50% of the cells are detached. The remaining attached cells are detached by gently tapping the culture vessel against a hard surface. The detached cells are resuspended in the freezing medium and centrifuged at 250×g for 5 minutes. The cells are resuspended in 2-3 ml of freezing medium clumps are disaggregated by gentle pipetting, and the cells are counted. The cell density is adjusted to $2-4 \times 10^5$ cells/ml and 1 ml aliquots are distributed into 1.2 ml capacity plastic freezing ampules. The ampules are placed into a styrofoam block in a $-85°$ C. freezer for 12-24 hours to freeze the cells at a controlled rate. The ampules are then removed from the styrofoam block and quickly transferred to liquid nitrogen storage.

EXAMPLE 4

Secondary cultures are initiated from the frozen suspensions of Example 3 and grown in the same medium under essentially the same conditions as described in Example 2 for primary cultures. Frozen ampules are removed from liquid nitrogen and thawed at 37° C. in 70% EtOH. Cells are inoculated at a density of 500-3000 cells/$cm^2$ into flasks containing preincubated stock culture medium. The medium is changed after 24 hours, and the resultant cultures are generally ready for further subculturing or preparation of inocula for clonal growth experiments after 4-7 days. The same criteria of maturity are used as for primary cultures, since growth of secondary cultures also tends to stop short of full confluency.

EXAMPLE 5

Clonal growth experiments are performed in 5 ml of medium in 60 mm petri dishes. The standard defined medium used for clonal experiments is MCDB153 supplemented with 5 ng/ml EGF, 5 g/ml insulin, 0.5 µg/ml hydrocortisone, 0.1 mM ethanolamine, and 0.1 mM phosphoethanolamine (See Table IV). In many cases, the calcium ion concentration in the medium is increased to 0.1 or 0.3 mM by adding appropriate volumes of 0.1M $CaCl_2$ in water.

The test media used in the clonal growth assays are prepared, placed into petri dishes (4.9 ml per 60 mm dish), and preincubated in the cell culture incubator for at least one hour while the cellular inoculum is being prepared.

Using the media and methods described in Examples 1-4, an inoculum of 25-50 cells/$cm^2$ can routinely be used (as contrasted with the at least 100 cells/$cm^2$ found necessary for satisfactory clonal growth when the inoculum was prepared from a stratified monolayer). The improved colony forming efficiency is due primarily to the use of a cellular inoculum prepared from cultures that are free of stratification and terminally differentiated cells. Such an inoculum can be prepared from primary cultures (Example 2) or secondary cultures (Example 4).

Alternatively, an effective inoculum can be prepared by destratification of primary cultures grown in a high serum medium by the Rheinwald, et al. feeder layer method. The growth medium is removed and the cells are washed twice with solution A and incubated for 24-48 hours in the defined clonal growth medium (Table II) with 0.03 mM $Ca^{++}$. This causes the terminally differentiated upper layers to delaminate, so that they can be mechanically dislodged from the firmly attached basal cells by vigorous pipetting and rinsing with solution A. The remaining basal cells in a monolayer population analogous to the basal layer in vivo are then used to prepare the inoculum for the clonal growth assay.

Cells from either of the above sources are released from their culture surface with trypsin-EDTA as described in Example 3. When the cells are detached, they are resuspended either in 10% wFBS in MCDB153 or in 0.1 soybean trypsin inhibitor plus 10% Vitrogen 100 in solution A and then centrifuged at 250×g for 5 minutes. The supernatant is removed by aspiration and the pellet is resuspended in 2-3 ml of unsupplemented MCDB153 and disaggregated to single cells by gentle pipetting. The cells are then counted and diluted in MCDB153 to either $1 \times 10^4$ or $5 \times 10^3$ cells/ml, and 0.1 ml of the cell suspension is added to each 60 mm dish containing 4.9 ml of test medium. The cultures are then incubated for 10-14 days at 37° C. with 5% $CO_2$ and saturated humidity. The medium is then removed and the colonies are fixed with 2% glutaraldehyde in 0.05M cacodylate buffer (pH 7.0) and stained with 0.1% crystal violet. Total colony area per petri dish is then determined with an Artek model 880 colony counter.

A. Effect of Stock Culture Conditions and Method of Preparing Cellular Inoculum (1) Two 60 mm petri dishes received inocula of 100 cells/$cm^2$ prepared from a stratified primary culture initiated with an irradiated 3T3 feeder layer and grown in 20% serum plus 0.4 µg/ml hydrocortisone.

(2) Two 60 mm petri dishes received inocula of 100 cells/$cm^2$ from a primary culture that was destratified prior to preparation of the inoculum.

(3) Two 60 mm petri dishes received inocula of 50 cells/$cm^2$ prepared from an unstratified serum-free secondary culture of cells that had been stored frozen between primary and secondary culture, as described in Example 3.

A clear improvement in colony forming efficiency was observed by use of an inoculum that is free of terminally differentiated cells [Procedures (2) and (3)]. The cultures of Procedure (1) yielded only a very limited number of colonies in the defined clonal growth medium. However, when the culture was first destratified [Procedure 2)], a comparable inoculum prepared from the remaining "basal" layer yielded far more colonies. The inoculum of Procedure (3) yielded a high colony-forming efficiency of greater than 20%.

B. Effect of Whole Bovine Pituitary Extract (wBPE) on Clonal Growth of Human Keratinocytes in Defined Medium Clonal growth assays were performed with a $Ca^{++}$ concentration of 0.03 mM and an inoculum of 50 cells/$cm^2$ with the following media variations: (1) MCDB153 plus wBPE at a protein concentration of 70 µg/ml; 2) MCDB153 plus defined supplements EGF, insulin, hydrocortisone, ethanolamine, and phosphoethanolamine at concentrations shown for clonal growth in Table IV; and (3) MCDB153 plus defined supplements plus wBPE at 70 µg/ml protein concentration.

This assay revealed that although wBPE alone will not support clonal growth in MCDB153 in the absence of the defined supplements [Procedure (1), it is appreciably beneficial when added to MCDB153 with a full set of defined supplements [Procedure (3)]. The greatest benefit from this undefined supplement is seen with a relatively sparse cellular inoculum (less than 50 cells per square centimeter) and at low calcium concentrations (0.03 mM) that are somewhat suboptimal for clonal growth in the defined medium.

C. Effect of Size of Cellular Inoculum, Calcium Concentration, and wBPE on Clonal Growth of Human Keratinocytes Clonal growth assays were performed in 60 mm petri dishes with cells from unstratified serum-free secondary cultures. Three media were employed: (1) MCDB153 with 0.03 mM $Ca^{++}$, defined supplements, and wBPE at 70 µg/ml protein; (2) MCDB153 with 0.03 mM $Ca^{++}$ and defined supplements, but no wBPE; and (3) MCDB153 with 0.3 mM $Ca^{++}$ and defined supplements, but no wBPE. In each medium, five densities of cellular inocula were employed: 12.5 cells/$cm^2$, 25.0 cells/$cm^2$, 37.5 cells $cm^2$, 50 cells/$cm^2$ and 100 cells/$cm^2$.

Three major effects were observed in this experiment. First, in the defined medium with an increased level of calcium (or at a low level of calcium with wBPE present), good clonal growth was obtained with an inoculum of 25 cells/$cm^2$. Second, overall growth in the defined medium without wBPE was increased dramatically by increasing the calcium ion concentration. However, the growth-promoting effect of wBPE does not appear to be due to bound calcium, since wBPE does not induce morphological changes comparable to those induced by elevated calcium, which are clearly evident even at relatively low magnification. Third, colony size decreases roughly in proportion to the increase in colony number as the inoculum is made larger.

Quantitative data from this experiment is shown in Table V. Each data point was an average of values from three dishes in duplicate experiments.

TABLE V

| Medium | Inoculated Cell Density (Cells/cm$^2$) | Colony Area (mm$^2$) |
|---|---|---|
| (1) | 12.5 | 130 |
| | 25.0 | 215 |
| | 37.5 | 325 |
| | 50.0 | 360 |
| | 100.0 | 475 |
| (2) $_a$ | 12.5 | 25 |
| | 25.0 | 115 |
| | 37.5 | 175 |
| | 50.0 | 250 |
| | 100.0 | 350 |
| (3) | 12.5 | 165 |
| | 25.0 | 225 |
| | 37.5 | 250 |
| | 50.0 | 305 |
| | 100.0 | 375 |

At all except the highest inoculum, defined medium with 0.3 mM Ca++ supports growth equivalent to that obtained by adding wBPE to a medium containing 0.03 mM Ca++. The leveling off of the total colony area curves at higher inocula clearly reflects the decrease in mean colony size in the more crowded cultures that is visually evident. This effect is seen under all defined conditions, at all Ca++ levels tested, and in the presence or absence of wBPE.

D. Effect of Calcium Concentration on Growth Rate and Colonial Morphology

Clonal growth assays were performed in defined medium with the calcium ion concentration and the cellular inoculum varied. The source and size of the cellular inoculum was (1) 100 cells/cm$^2$, derived from a destratified serum-grown primary culture initiated with a 3T3 feeder layer; and (2) 50 cell/cm$^2$, derived from a serum-free secondary culture after recovery from frozen storage. For both procedures (1) and (2), the calcium ion concentration was varied: 0.03 mM; 0.1 mM; 0.3 mM; and 1.0 mM.

The ability of calcium ion concentration to control expression of keratinocyte differentiation under fully defined conditions is demonstrated in the cultures of both procedures (1) and (2). Similar results are obtained whether the inoculum is prepared from a destratified serum-grown primary culture originally established by the method of Rheinwald, et al. (1) or from a secondary culture initiated, frozen, and recovered from frozen storage under serum-free conditions (2). In either case, stepwise increase in calcium concentration from 0.03 mM to 1.0 mM causes distinctive changes in colony morphology and growth rate that appear to be directly related to the extent of stratification and terminal differentiation. A few poorly growing diffuse colonies of fibroblast-like cells were observed at the highest calcium concentration but were absent at lower calcium concentrations.

EXAMPLE 6

Preliminary experimental work is ongoing to develop an optimal combination of keratinocyte cells grown in the stock culture, frozen storage and clonal growth media and a suitable support matrix vehicle to transport the cells onto a damaged area of skin and fix the cells there to promote revascularization and epithialization.

One such preliminary study employs the multilayer collagenous matrix of Yannas, et al., U.S. Pat. No. 4,060,081. Liquid medium MCDB153 was prepared and supplemented as described in Example 1 for clonal growth except that EGF concentration was increased to 10 μg/ml. The matrix was placed into the dish containing the medium. A suspension of ingle human keratinocyte cells at an inoculation density of approximately 1.25 × 10$^3$ cells/cm$^2$ was inoculated into the dish.

The dish containing cells, medium and matrix are incubated for between ten and thirty days at 37° C. After incubation for thirty days, keratinocyte attachment and proliferation was observed on the surface of the collagen-GAG layer of the membrane. Studies directed at quantification of cell growth on the matrix and use of other biodegradable vehicles for transport of the cells are presently being conducted.

Numerous modifications and variations in the invention are expected to occur to those skilled in the art upon consideration of the foregoing description. Consequently, only such limitations as appear in the appended claims should be placed on the invention.

What is claimed is:

1. A population of human epidermal cells growing in a transferrin-free medium comprising:
   complete MCDB153;
   epidermal growth factor at a concentration of 1.0 ng/ml to 25.0 ng/ml; and
   insulin at a concentration of 0.5 μg/ml to 2. A population of cells as in claim 1 wherein said medium additionally comprises at least one supplement selected from the group consisting of:
   hydrocortisone at a concentration of 0.14 μM to 28.0 μM;
   ethanolamine at a concentration of 0.01 mM to 1.0 mM;
   phosphoethanolamine at a concentration of 0.01 mM to 1.0 mM;
   calcium chloride at a concentration of 0.03 mM to 1.0 mM; and
   whole bovine pituitary extract at a protein concentration of 7.0 μg/ml to 700.0 μg/ml.

3. A population of human epidermal cells as in claim 1 wherein said cells have formed a monolayer or multiple strata in said medium.

* * * * *

UNITED STATES PATENT AND TRADEMARK OFFICE
CERTIFICATE OF CORRECTION

PATENT NO. : 4,940,666
DATED : July 10, 1990
INVENTOR(S) : Steven T. Boyce and Richard G. Ham It is certified that error appears in the above-identified patent and that said Letters Patent is hereby corrected as shown below:

On the title page first-named inventor is as follows:

--Steven T. Boyce--

IN THE TITLE

Amend the title to read: --HUMAN EPIDERMAL CELL POPULATIONS IN A TRANSFERRIN-FREE MEDIUM--.

IN THE CLAIMS

Claim 1, line 6, column 16, line 42, after "to" insert --50.0 µg/ml--.

Signed and Sealed this

Thirteenth Day of August, 1991

Attest:

HARRY F. MANBECK, JR.

Attesting Officer

Commissioner of Patents and Trademarks